United States Patent
Mayo Martin

(10) Patent No.: US 9,750,600 B2
(45) Date of Patent: Sep. 5, 2017

(54) BREAST IMPLANT

(71) Applicant: Federico Mayo Martin, Madrid (ES)

(72) Inventor: Federico Mayo Martin, Madrid (ES)

( * ) Notice: Subject to any disclaimer, the term of this patent is extended or adjusted under 35 U.S.C. 154(b) by 0 days.

(21) Appl. No.: 14/442,933

(22) PCT Filed: Nov. 11, 2013

(86) PCT No.: PCT/ES2013/070782
§ 371 (c)(1),
(2) Date: May 14, 2015

(87) PCT Pub. No.: WO2014/076339
PCT Pub. Date: May 22, 2014

(65) Prior Publication Data
US 2015/0313708 A1    Nov. 5, 2015

(30) Foreign Application Priority Data

Nov. 16, 2012  (ES) .................................. 201231778

(51) Int. Cl.
*A61F 2/12*    (2006.01)

(52) U.S. Cl.
CPC ........ *A61F 2/12* (2013.01); *A61F 2220/0008* (2013.01); *A61F 2250/0098* (2013.01)

(58) Field of Classification Search
USPC .................................. 623/7, 8, 23.64–23.67
See application file for complete search history.

(56) References Cited

U.S. PATENT DOCUMENTS

| 6,203,570 | B1* | 3/2001 | Baeke ....................... A61F 2/12 |
| | | | 623/7 |
| 9,393,106 | B2* | 7/2016 | Van Epps ................. A61F 2/12 |
| 2004/0249457 | A1* | 12/2004 | Smith ....................... A61F 2/12 |
| | | | 623/7 |
| 2005/0080338 | A1* | 4/2005 | Sirimanne ............ A61K 49/006 |
| | | | 600/431 |

\* cited by examiner

*Primary Examiner* — Yashita Sharma

(57) ABSTRACT

Breast implants with anatomical morphology have the problem of possibly rotating from their implantation position in the patient's body, which causes an aesthetic anomaly. With the implant of the invention, this problem is resolved, owing to the arrangement of silicone strips (5-8) fixed to the frontal face (2) and/or to the rear face (3) of silicone cover of the implant. The strips are provided at their free end with respective orifices (7, 9) for the passage of a suture point, such that these suture points enable the implant to be fixed to the corporal tissue of the user, such as for example to the breast tissue, to the pectoralis major muscle, to the fascia of the pectoralis major muscle, etc., the implant thus remaining immobilized. The implant also includes a mark (10) made of radiological material which enables the position of the implant in the patient's body to be checked by means of conventional radiology or other means.

5 Claims, 2 Drawing Sheets

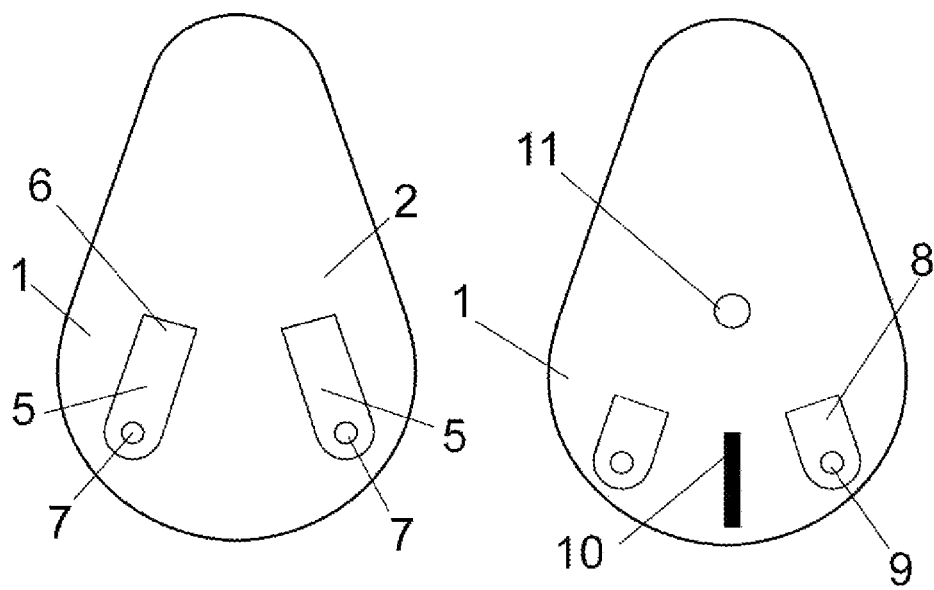
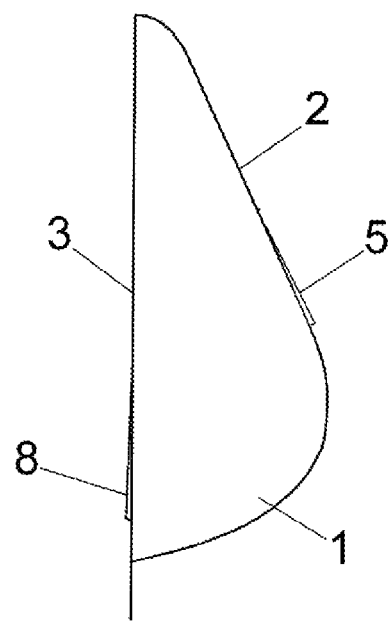

BREAST IMPLANT

FIELD OF THE INVENTION

The invention relates to a breast implant used in prosthetic surgery, and more specifically aesthetic breast surgery, such as augmentation mammoplasty and the reconstruction of the breasts following the removal of mammary glands due to any type of health problem or another type of problem.

BACKGROUND

Breast implants with anatomical morphology can be filled with silicone gel or physiological saline. In some cases, the filling is a mixture of silicone gel and saline. The surface which surrounds this filling, whatever it may be, is called the cover. The cover is made by adding silicone layers and leaving them to dry. Each manufacturer has its own way of making the cover, although the standard is that the final surface in these anatomical implants is texturized. There are manufacturers who add a polyurethane cover to this texturization. In the case in which the anatomical implants are used as expanders with the aim of reconstructing the post-mastectomy breast, these have on their rear face a valve with a metallic component which allows their positioning from the exterior and the filling in series by means of transcutaneous injections.

Smooth anatomical implants are not commercialized since their surface would not be adherent and they would have displacements or rotations in all cases. In the case of the texturized anatomical breast implants, the pore of the texturization itself produces an adherent effect which prevents rotations in some cases but not in all. The deeper the pore, the more aggressive the texturing, and the greater theoretic adherence it has. However, deeper pores also have more problems over the medium and long term such as delayed seroma and capsular contracture.

For these reasons, an anatomical implant may be micro-texturized. However, micro-texturized anatomical implants rotate more frequently, although they have few incidences of capsular contracture and delayed seroma.

The surgical technique wherein a dissection is entirely customized to the anatomical implants offers fewer rotations over the short and medium term.

In many cases, although the surgeon carries out a dissection customized to the implant, there are factors inherent to the particular patient, such as the elasticity of the tissue or physical exercise which cause the dimensions of this pocket to become modified with time and thus cause rotations of the implants.

On the other hand, the fact that these anatomical implants usually rotate, causes many surgeons all over the world to not use them regularly in spite of the fact that the aesthetic results are always more natural when the surgery is carried out with these implants compared to the results of other round implants.

There are no real statistics available for the percentage of rotations or the average degree which an implant rotates since the manufacturers do not add any device to the anatomical implants which may facilitate the detection, from the exterior of the patient, of this hypothetical rotation over the medium and long term.

All of the rotations of anatomical implants are resolved by an additional surgical intervention when this rotation is not resolved by external maneuvers. In the majority of the cases, the external maneuvers do not resolve the rotation and the patient has to return for surgical intervention.

In the cases of minor rotations, many times these are tolerated because the deformity is minimal and the patients prefer to accept a minor deformity and thus avoid reintervention.

Thus, in the field of breast implants with anatomical morphology, there are currently two problems:

The rotation of the implants

Lack of means for allowing, from the exterior by way of a radiological exam or similar, to check whether the implant is positioned correctly or whether, on the contrary, it has rotated.

SUMMARY

The present invention may provide a breast implant, in particular a breast implant with anatomical morphology which is structured so as to reduce the problems of rotation which these implants over the medium and long term.

This may be achieved by fixing the implant to the body of the patient by use of simple suture points.

The inventive breast implant may resolve the two existing problems of known methods described above.

To this end, the inventive implant may be defined, proceeding from the classic structure of a breast implant with anatomical morphology, by novel structures in the cover of the implant which serve as a mechanism for fixing said implant in its optimum position relative to the body of the patient, by means of simple suture points, thereby preventing rotation of the implant over the medium and long term.

In one particular embodiment, the novel structures include rectangular strips of the same material as the cover, e.g., solid silicone, with the same resistance, flexibility, elasticity and/or elongation properties inherent to the silicone of which the cover is made.

These rectangular structures, duly fixed to the implant, for example by means of a sealant or sealing similar to that which occludes the filled pore located on the rear part, have a distal orifice or throughhole which allows the passage of a suture point for fixing to the suitable tissue of the patient. The implant preferably has four fixing strips or structures, two on its front face and two on its rear face, each with a length of approximately 2 cm and a width of between 6 and 8 mm.

According to another of the features of the invention and in order to enable the external check of the position of the implant once it has been inserted, the implant may include a mark with a radiopaque biocompatible material base, for example titanium, which is located on the tactile mark that conventional implants have at the lower pole. This enables the position of the implant to be determined at any time by means of conventional radiology or any other suitable similar means.

DESCRIPTION OF THE DRAWINGS

In order to complement the description which follows and with the aim of aiding a better understanding of the characteristics of the invention, in accordance with a preferred practical exemplary embodiment of the same, a set of drawings accompanies said description as an integral part thereof, in which the following is depicted in an illustrative and non-limiting manner:

FIG. 3 shows a front elevation view of one embodiment of a breast implant of the present invention.

FIG. 4 shows a rear elevation view of the same implant of FIG. 3.

FIG. 5 shows a profile view of the implant of FIGS. 3 and 4.

DESCRIPTION OF EXAMPLE EMBODIMENT

Figure 1:
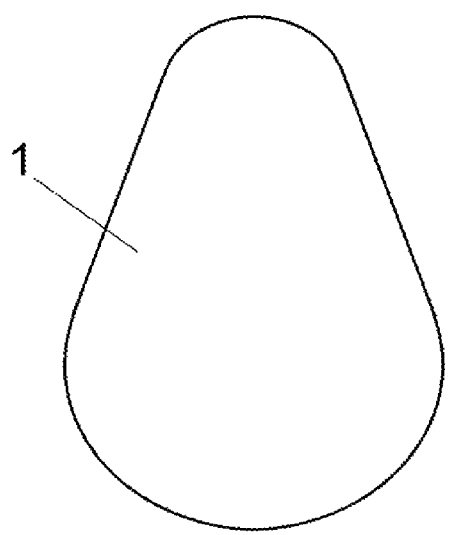
FIGS. 1 and 2 show respective schematic depictions of a breast implant with conventional anatomical morphology, the first in a frontal view and the second in profile or lateral view.
Figure 2:
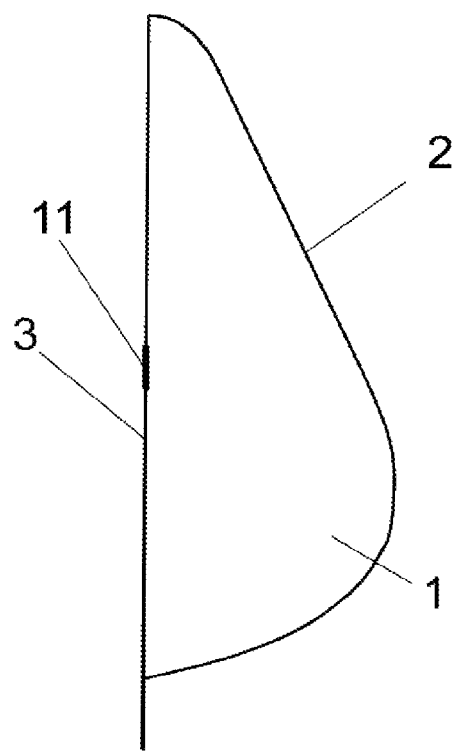

One embodiment of the inventive breast implant, as depicted in FIGS. 3 and 5, includes a body (1) with anatomical morphology, matching the breast implant of FIGS. 1 and 2 for a same patient in form and dimensions, that is to say, by means of an enveloping or hermetically closed cover which houses in its interior a filling of silicone gel and/or saline, which has an orifice (11) on the rear part for the silicone filling which is sealed at rear, defining a front face (2) and a rear face (3).

In accordance with the invention, the body (1) of the implant includes on a lower portion of its frontal face two strips (5) of the same material as the cover, for example, solid silicone. Strips (5) may be symmetrically positioned with respect to the imaginary vertical and medial axis of the implant, as shown in FIG. 3. For example, strips (5) may be mirror images of each other with respect to an imaginary vertical plane bisecting body (1). Proximal ends (6) of strips (5) may be fixed to the frontal wall (2) of the implant cover by means of a sealant, sealing or permanent adhesive (e.g., biological adhesive). The distal ends of strips (5) may each include a respective orifice or throughhole (7) which allows the passage therethrough of suture.

On the rear face (3) of the implant has a structure similar to that of the front face (2). Specifically, two other strips (8) are fixed to the rear wall (3) of the cover and each strip (8) includes a respective orifice or throughhole (9) at its distal end for allowing the passage of suture. Proximal ends of strips (8) may be fixed to the rear wall (3) of the implant cover by means of a sealant, sealing or permanent adhesive (e.g., biological adhesive).

In one particular embodiment, the strips (5, 8) may be rectangular and may have a length of approximately 2 cm and a width of between 6 and 8 mm to provide good feel and resistance.

The tissue to which said strips (5, 8) are attached (e.g., by suture) may be breast tissue, the pectoralis major muscle, the fascia of the pectoralis major muscle, the fascia of the anterior rectus muscle, or the fascia of the intercostal muscles. The tissue to which said strips (5, 8) are attached may depend upon the space where the implant is inserted, subglandular, subfascia or subpectoral or dual plane, and on the approach for inserting them, periareolar or inframammary or even axillar.

In one embodiment, the inventive breast implant may include a mark (10) with a radiopaque biocompatible material base, preferably on the tactile element or mark which the implants include at their lower end or lower pole, which enables the position of said implant to be determined at any time by means of conventional radiology, mammography or scanner or ultrasound.

The invention claimed is:

1. A breast implant having anatomical morphology, the breast implant comprising:
   a silicone cover having an exterior surface;
   a filling within the cover; and
   at least two strips, each strip having a proximal end and a distal end, each proximal end being attached to a lower half of the exterior surface of the cover such that one of the at least two strips is symmetrically disposed opposite another of the at least two strips about a vertical axis of the implant, each distal end including a throughhole configured to receive suture therein for attaching the implant to tissue of a body of a patient.

2. The breast implant according to claim 1, wherein the at least two strips comprise four strips, two of the four strips being attached to a front face of the cover, and two other of the four strips being attached to a rear face of the cover.

3. The breast implant according to claim 1, wherein the at least two strips are rectangular shaped, have a width of between 6 mm and 8 mm and a length longer than the width, and are attached to the cover by a biological adhesive.

4. The breast implant according to claim 1, further comprising:
   a tactile element on the lower half of the exterior surface of the cover; and
   a mark formed of a radiopaque biocompatible material, the mark being superimposed on the tactile element.

5. The breast implant according to claim 4, wherein the radiopaque biocompatible material comprises titanium.

* * * * *